(12) United States Patent
Gratton et al.

(10) Patent No.: US 9,167,970 B2
(45) Date of Patent: Oct. 27, 2015

(54) NON-INVASIVE OPTICAL IMAGING FOR MEASURING PULSE AND ARTERIAL ELASTICITY IN THE BRAIN

(75) Inventors: Gabriele Gratton, Champaign, IL (US); Monica Fabiani, Champaign, IL (US); Kathy Low, Champaign, IL (US); Edward Maclin, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 294 days.

(21) Appl. No.: 13/504,401

(22) PCT Filed: Oct. 14, 2010

(86) PCT No.: PCT/US2010/052750
§ 371 (c)(1),
(2), (4) Date: Apr. 26, 2012

(87) PCT Pub. No.: WO2011/059632
PCT Pub. Date: May 19, 2011

(65) Prior Publication Data
US 2012/0215114 A1    Aug. 23, 2012

Related U.S. Application Data (60) Provisional application No. 61/256,024, filed on Oct. 29, 2009.

(51) Int. Cl.
*A61B 5/00* (2006.01)
*A61B 5/02* (2006.01)

(52) U.S. Cl.
CPC ........... *A61B 5/0059* (2013.01); *A61B 5/02007* (2013.01); *A61B 5/02028* (2013.01); *A61B 5/7207* (2013.01)

(58) Field of Classification Search
CPC ............ A61B 5/0059; A61B 5/02007; A61B 5/02028; A61B 5/7207
USPC .................. 600/473, 476, 407, 481; 382/128
See application file for complete search history.

(56) References Cited

U.S. PATENT DOCUMENTS

| 3,646,931 A * | 3/1972 | Phelps et al. ................. 600/502 |
| 2006/0058683 A1 * | 3/2006 | Chance ......................... 600/476 |

(Continued)

OTHER PUBLICATIONS

Hu et al., "Inferring Cerebrovascular Changes from Latencies of Systemic and Intracranial Pulses: a Model-Based Latency Subtraction Algorithm", J Cereb Blood Flow Meta., Apr. 2009, vol. 29, pp. 688-697.*

(Continued)

*Primary Examiner* — Katherine Fernandez
(74) *Attorney, Agent, or Firm* — Yakov Sidorin; Quarles & Brady LLP (57) ABSTRACT

An optical imaging system and a method for generating a report regarding elasticity of arteries in the brain of a subject under test. Light output from the light source of the imaging system non-invasively illuminates at least one blood vessel or region of interest in the brain and, upon the interaction with the vessel, is registered with an optical detector to obtain a shape parameter of a hemodynamic pulse in the vessel. The shape parameter is further correlated to an elasticity parameter of the blood vessel(s) feeding the brain region of interest and presented in a form of report that may be a two- or a three-dimensional image of the parameter across the tested region of the brain.

16 Claims, 7 Drawing Sheets

(56) References Cited

U.S. PATENT DOCUMENTS

2007/0287899 A1 12/2007 Poupko
2010/0016732 A1* 1/2010 Wells et al. .................. 600/476

OTHER PUBLICATIONS

The International Search Report and Written Opinion as mailed on Apr. 8, 2011 for International Application No. PCT/US2010/052750.
Millasseau. S.C, et al., "Determination of age-related increases in large artery stiffness by digital pulse contour analysis," Clinical Science, vol. 103, No. 4, Oct. 1, 2002, pp. 371-377, XP002617169.
Edward L Maclin, et al., "Improving the signal-to-noise ratio of event-related optical signals," IEEE Engineering in Medicine and Biology Magazine, IEEE Service Center, Piscataway, New Jersey, vol. 26, No. 4, Jul. 1, 2007, XP011187353.
Theodore J Huppert, et al., "Chapter 14. Noninvasive Imaging of Cerebral Activation with Diffuse Optical Tomography," Jan. 1, 2009, In Vivo Optical Imaging of Brain Function, CRC Press, Boca Raton, US., pp. 393-433, XP009143168.

Gabriele Gratton, et al., "Principles, Methods, and Experimental Results," Jan. 1, 2009, In Vivo Optical Imaging of Brain Function, CRC Press, Boca Raton, US, pp. 435-460, XP009143146.
Nichols WW, et al., "Effects of arterial stiffness. pulse wave velocity, and wave reflections on the central aortic pressure waveform," Journal of Clinical Hypertension, Elsevier, New York, NY, US, vol. 10, No. 4, Apr. 1, 2008, pp. 295-303, XP007916725.
Page R. Painter, "The velocity of the arterial pulse wave: a viscous-fluid shock wave in an elastic tube," Theoretical Biology and Medical Modelling, Jul. 29, 2008, pp. 1-6, 5:15, BioMed Central Ltd.
Gabriele Gratton, et al, "Removing the heart from the brain: Compensation for the pulse artifact in the photon migration signal," Psychophysiology, 32, 1995, pp. 292-299, Cambridge University Press, US.
James J. Oliver, "Noninvasive Assessment of Arterial Stiffness and Risk of Atherosclerotic Events," Arteriosclerosis, Thrombosis, and Vascular Biology, 2003, 23, pp. 554-566, American Heart Association, Dallas, Texas, U.S.

* cited by examiner

NON-INVASIVE OPTICAL IMAGING FOR MEASURING PULSE AND ARTERIAL ELASTICITY IN THE BRAIN

CROSS-REFERENCES TO RELATED APPLICATIONS

This application represents the national stage entry of PCT International Application No. PCT/US2010/052750 filed on Oct. 14, 2010 and claims the benefit of U.S. Provisional Patent Application Ser. No. 61/256,024 filed on Oct. 29, 2009. The above-referenced patent applications are incorporated herein by reference in their entirety.

STATEMENT REGARDING FEDERALLY SPONSORED RESEARCH OR DEVELOPMENT

This invention was made with support under The National Institutes of Health (NIH) grant AG021887. The United States Government has certain rights in the invention.

TECHNICAL FIELD

The present invention relates to systems and methods for performing studies of brain tissue and, in particular, to optical systems and methods for measuring elasticity of arteries in the brain.

BACKGROUND ART

Normal aging is accompanied by a number of cognitive changes, including decline in working memory and executive function/attention control, as well as in long-term memory and speed of processing. These normal age-related declines in cognitive functions are exacerbated in those older adults who suffer from mild cognitive impairment (MCI), which, according to the American College of Physicians, affects about 20% of the population over 70 years old. Beyond this class of individuals suffering from MCI, some among the older population develop Alzheimer's disease or other forms of dementia. An estimated 26.6 million people worldwide had Alzheimer's in 2006 and this number may quadruple by 2050. Increasing knowledge about possible predictors of age-related cognitive impairments and their interactions, providing means of early detection, and improving the chances of successful prevention and/or treatment of the impairments can yield substantial societal and economic benefits.

Recent work with human and animal subjects suggests that cardiopulmonary (aerobic) fitness is one such predictor, and that increased level of fitness can slow down or even reverse some of the cognitive effects of aging. For example, highly-fit older adults were shown to have more preserved white and grey matter in brain areas susceptible to age-related loss, such as frontal, parietal, and temporal cortex. The same older adults demonstrate increased performance in neuropsychological and cognitive tasks compared to age and gender-matched low-fit older adults. Highly-fit older adults also display patterns of brain function that are similar to those of younger adults. Finally, sedentary older adults who undergo a 6-month exercise intervention have been shown to improve in all of these aspects of cognitive health—brain anatomy, function and behavioral measure of performance. Measurements of brain function provide invaluable information for these purposes. Cerebrovascular function is particularly informative in this respect and can be viewed as a complex phenomenon in which different cerebrovascular compartment, such as large arteries, regional arteries, arterioles and capillaries, play interdependent roles.

One measure of the cerebrovascular health is stiffness or, alternatively, elasticity of arteries in the brain. Arterial stiffness may be correlated with cognitive aging as well. Generally, data representative of arterial stiffness may be obtained through measurements of pulse in a given artery. Therefore, imaging of the brain can be performed to obtain spatial brain maps containing data that represent arterial stiffness in order to facilitate the understanding of different cerebrovascular compartments, different aspects of brain anatomy and function, and complex profiling of the cognitive function of the brain.

Traditionally, studies of brain function in human subjects rely on surface measurements of electrical potentials, such as electroencephalogram, or EEG, ultrasound, functional magnetic resonance imaging (fMRI), or various tomographic techniques such as computer X-ray tomography (CT) or positron emission tomography (PET). All these techniques are powerful and have some advantages, but they suffer from drawbacks that limit their use as continuous, non-invasive, portable, and low-cost medical monitors. For example, EEG can be inaccurate and does not lend itself to creating accurate spatial maps. On the other hand, while PET and fMRI lend themselves to providing useful spatial maps of changes in brain functions, such as metabolism or blood flow, fMRI requires high-energy magnetic fields and PET data cannot be obtained quickly enough for informative comparison with other type of data. Furthermore, PET requires the use of a radionuclide or radiopharmaceutical, which can be undesirable. Likewise, CT requires the use of an ionizing radiation, which can also be undesirable.

Conventional non-invasive methods of characterizing the brain arteries, specifically, blood-flow velocity and direction, include transcranial Doppler (TCD) ultrasonography. However, ultrasound-based methods, such as TCD, produce only localized images and do not lend themselves to spatial mapping. Furthermore, TCD is often disfavored in clinical settings due to the level of interference presented by the skull bones that significantly deform and disperse the propagation of the ultrasound waves thus making it complicated to provide localized estimates of intracranial structures. Rather, when utilizing ultrasound to study arterial stiffness, the ultrasound analysis methods are typically limited to localized studies of arteries providing blood flow to the brain, such as arteries in the neck.

It is desirable, therefore, to have a system and method for studying the performance of brain blood vessels, including vessel stiffness, for the purpose of characterization of vascular health of the brain that does not suffer from the above-described drawbacks of traditional imaging systems.

SUMMARY OF THE INVENTION

According to one embodiment of the invention, a method for generating a report regarding an elasticity of arteries in a brain is provided. The method includes illuminating at least one blood vessel in the brain with light emitted by a light source of an optical imaging system and registering light that has interacted with at least one blood vessel in the brain with an optical detector of the optical imaging system to obtain data that represents interaction between the light and the at least one blood vessel. The method further includes using the obtained data to determine a shape parameter of a hemodynamic pulse in at least one blood vessel in the brain. The shape parameter is further correlated to an elasticity parameter of blood vessels in the brain and a report, indicating the elasticity parameter, is generated.

Illumination of at least one blood vessel is preferably non-invasive, and a determination of the shape parameter of a hemodynamic pulse according to the method of the invention may include a determination of pulse latency. Further, a report indicating the elasticity parameter may include either a two-dimensional or a volumetric image or, alternatively, a video sequence of two-dimensional images that represents the propagation of the pulse across the region of the brain.

According to another embodiment of the invention, an imaging system is provided that includes an illumination system configured to illuminate a region of interest (ROI) of a subject with photons and receive the photons that traversed the ROI between the source of light and a detector and interacted with the ROI having at least one blood vessel and an input for analyzing the photons after interaction with the ROI to compile imaging data. The imaging system also includes a processor transforming the imaging data to determine a shape parameter of a hemodynamic pulse in at least one blood vessel and a graphical output, in which appears a display of at least one image representing the shape parameter.

According to yet another embodiment of the invention, a computer program product is provided for use on a computer system for creating an image of a region of a brain of a subject under test, the computer program product comprising a computer usable medium having a computer readable program code therein, which, when loaded into the computer system, establishes an apparatus, implemented in the computer system. This apparatus includes an input for receiving digital data representing interaction between light and at least one blood vessel in the region of the brain, the data being acquired by non-invasively illuminating at least one blood vessel with light emitted by at least one light source and registering, with at least one optical detector, the light that has interacted with at least one blood vessel. The apparatus also includes a processor for transforming the input digital data to determine a shape parameter of a hemodynamic pulse in at least one blood vessel and a graphical output, in which appears a display of at least one image representing the shape parameter.

BRIEF DESCRIPTION OF THE DRAWINGS

The foregoing features of the invention will be more readily understood by reference to the following detailed description taken in reference to the accompanying, drawn not-to-scale, figures where like features and elements are denoted by like numbers and labels, and in which:

FIG. 5(A-C) are image-maps derived from pulse measurement data and representing the duration of the systolic pressure wave across the brain for different subjects under test;

DETAILED DESCRIPTION OF SPECIFIC EMBODIMENTS

Recent advances in brain imaging studies suggest that understanding brain arterial stiffness or, alternatively, arterial elasticity can be a powerful indicator of cerebrovascular disease. The present invention provides a system and method for the incorporation of pulse data in brain mapping obtained with the use of diffusive optical methods to provide information about vascular health of different regions of the brain. Accordingly, a three-dimensional (3D) brain-mapping technique of the present invention makes use of optical tomography (OT) or diffuse OT (DOT) to acquire data associated with propagation of the pulse waveform through the brain.

Optical tomography and, in particular, DOT are centered around the idea that light passes through a body in small amounts and emerges bearing clues about tissues through which it has passed. These optical methods utilize non-ionizing NIR light, which is well tolerated in large doses by brain tissue, and have been recognized by some as a preferred non-invasive diagnostic technique due to their potential low cost and very little side effects.

In conventional techniques for brain imaging and creating maps of the brain using OT or DOT, pulse data is intentionally disregarded as an impediment to brain mapping. Indeed, these optical methods are known to be highly sensitive to blood pulsation in small blood vessels. As a result, the pulse signal in OT or DOT has been viewed as unavoidable noise and special procedures to remove the pulse signal from the brain maps have been developed. Contrary to conventional views, the present invention utilizes data representing the propagation of the hemodynamic pulse-wave in the brain and collected with the use of appropriately configured DOT or another diffusive optical method.

Embodiments of the invention stem from the realization that arterial elasticity (which is the inverse of arterial stiffness) determines a prolongation of the systolic phase of the pulse (which is the phase during which blood is maximally pushed through the arteries) with respect to the diastolic phase (which is the phase during which blood is minimally pushed through the arteries). The systolic phase is characterized by a decrease in the intensity of light going through a voxel and the diastolic phase by an increase. (It is appreciated that in a related embodiment employing de-oxyhemoglobin concentration as a reference parameter characterizing the vascular health of the brain, the relationship is reversed, i.e. the corresponding detected light intensity increases during the systolic phase and decreases during the diastolic phase). Based on the analysis of the time-progression of the pulse-wave in the brain, embodiments of the invention allows for determination of the arterial stiffness.

According to the invention, the intracranial origin of the pulse signal can be established by comparing pulse signals obtained from different optical source/optical detector pairs characterized by different distances separating a source and a detector of the pair. Alternatively or in addition, the intracranial origin of pulse data can be confirmed by comparing the results of the measurements collected in two different fashions one of which utilizes, for example, the amplitude modulation of the light output of the optical source(s) and another utilizes a phase-delay measurement which can be obtained if a frequency-domain optical imaging system is used.

Embodiments further allow for indirect estimation of the duration of the pulse obtained for each location in the brain based on parameterization of two-dimensional (2D) or volumetric (3D) images generated with the use of a processor and providing models of the brain. Because the pulse duration relates to elasticity of the arteries, and inversely relates to arterial stiffness, these 2D or 3D reconstructed images are also interpreted to reveal arterial elasticity, or compliance, that is an important indicator of cardiovascular health. The results of such interpretation are stored, on a non-transient tangible computer-readable storage medium and may be further displayed to the user in a form of a graphical output from the computer-based system, for example. As a result, the invention enables non-invasive optical brain mapping technology providing critical information about cerebrovascular function of the brain.

Embodiments of the present invention have been implemented in studies of aging demonstrating that high-fitness older adults have elasticity of brain arteries similar to that of younger subjects and different from that of low-fitness older counterparts. The present invention includes and is implemented in a system, a method, and a computer-program product including program code for transforming the pulse-related brain-mapping data that represents a propagation of the hemodynamic pulse across the brain to 2D and 3D imaging representation of hemodynamic patterns in the brain. The term "image" generally refers to an ordered representation of detector signals corresponding to spatial positions. For example, an image may be an array of values within a tangible electronic memory, or, alternatively, a visual image may be formed on a display device such as a video screen or printer.

Figure 1:
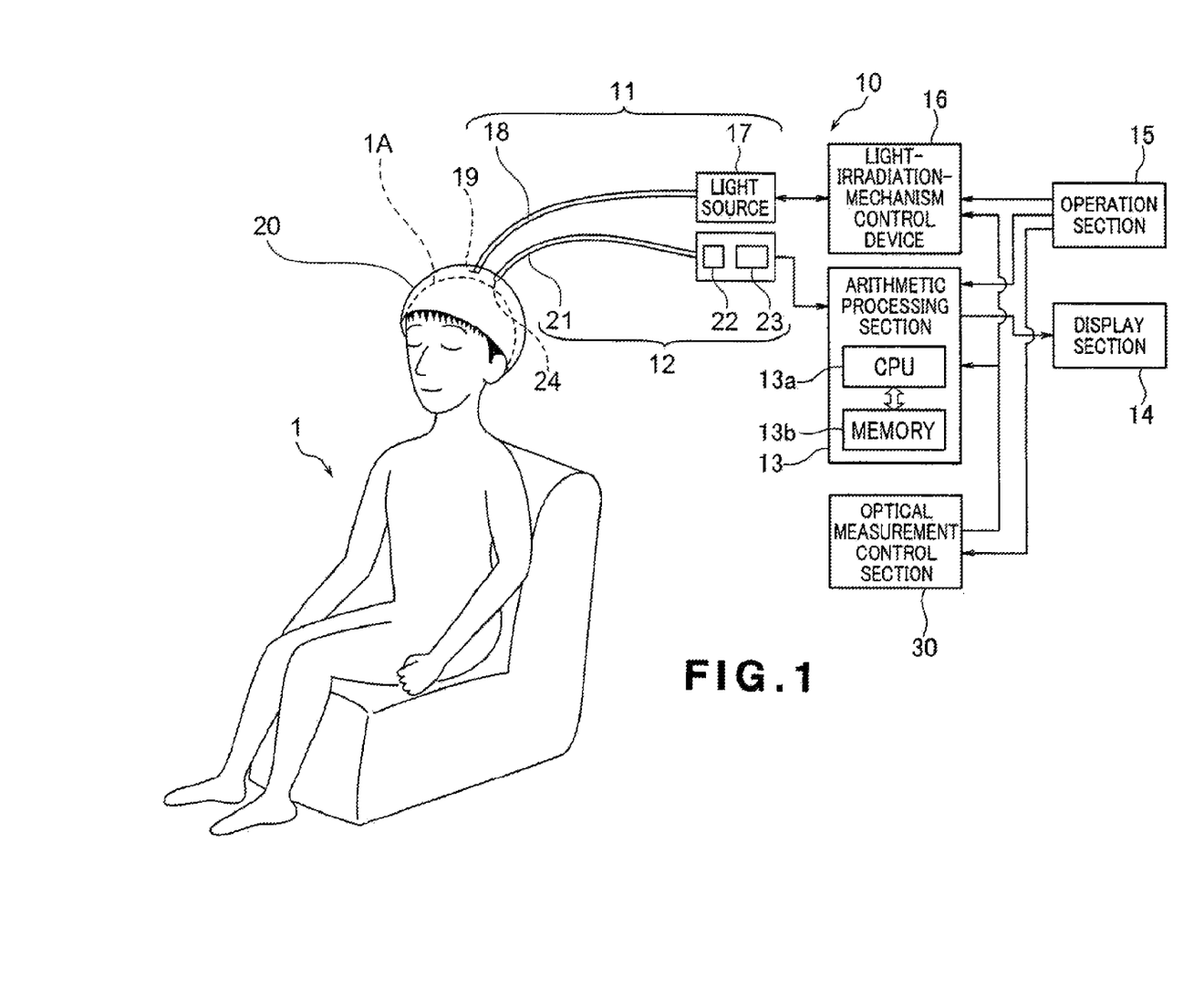
FIG. 1 is a schematic representation of a system in accordance with an embodiment of the present invention.

Turning now to FIG. 1, a system 10 is provided showing schematically a general setup of an optical measuring apparatus in accordance with an embodiment of the present invention. The system 10 includes illumination means configured to illuminate a region of interest (ROI) with light and detecting means configured to discover the existence of light that has interacted with the ROI. In one embodiment, illuminations means include a light irradiation mechanism 11 and a light-irradiation control device 16, and detecting means include a light detection mechanism 12. In addition, the system 10 has computer-processing means such as an arithmetic processing section 13 that includes a processor, a non-transient tangible computer-readable storage medium, and reporting means such as a display or a graphical output 14, an operational section 15, and an optical measurement control section 30. The optical measurement control workstation 30 controls measuring operations of the optical measuring apparatus 10.

The light irradiation mechanism 11 irradiates a desired portion such as a head of a person who is subject to the measurement. The light irradiation mechanism 11 includes a light source 17 emitting light in an appropriate portion of the spectrum, for example in the near infrared (NIR) range, and a plurality of optical fibers 18 that transmit the light emitted by the light source 17. As illustrated, the optical fibers 18 are connected at one end to the light source 17 and at the other end fixed to a helmet 20. It should be noted that although only two emission optical fibers 18 are shown in order to simplify the drawing, in practice any number of emission optical fibers 18 may be used. The light source 17 may be in the form of a monochromatic light source, such as a semiconductor laser or light emitting diode, halogen lamp, tungsten lamp or other light source capable of outputting light of wavelengths in the near infrared range. In an alternative, light emitted by a light source having a continuous spectrum may be filtered via a plurality of filters, such as interference filters each allowing light of a single wavelength to pass therethrough. It shall be understood that although generally the irradiation of the brain may be carried out with a plurality of wavelengths, the operation of the system of the invention at a single wavelength is also contemplated.

The helmet 20 forms a cover member to which the light-irradiating section 19 of the optical fibers 18 and a later-described detection optical fiber 21 of the light detection mechanism 12 are fixed. In other words, the helmet 20 is a unit for placing and holding the optical fibers 18 and the like of the optical measuring apparatus 10 in sufficient proximity to the measured portion 1A of the head and in fixed positional relation to the latter. Again, it should be noted that although only two detection optical fibers 21 are shown in order to simplify the drawing, in practice any number of emission optical fibers 21 may be used.

The light detection mechanism 12 includes the detection optical fibers 21 for collecting, through the light-collecting section 24, and transmitting the diffuse/scattering-based reflected light from the measured portion of the head, a photo-detector, for example, photo-diode or photoelectron multiplier sensitive to a plurality of different wavelengths, and a signal processing section 23. The signal processing section 23 of the light detection mechanism 12 converts the light, detected by the photo-detector 22, into an electrical signal. The converted electrical signal is then passed to the arithmetic processing section 13.

The arithmetic processing section 13, which may comprise a computer including a CPU 13a and tangible computer-readable storage medium such as memory 13b, performs given arithmetic operations on data representative of the diffuse and/or scattered reflected light detected via the light detection mechanism 12, to transform these data, as will be described, by calculating desired parameters related to blood in the measured portion of the head. As will also be described, an output from the processing section 13 such as an image, a tangible report, or other such information is then sent to the output section 14 to be graphically displayed or otherwise presented to the operator.

The operation section 15 is an input means operable to make necessary settings and change a designated program and measuring parameters in the optical measuring apparatus 10. Via this operation section 15, the operator can perform an input operation to provide necessary control instructions to the arithmetic processing section 13, the light-irradiation-mechanism control device 16, the optical measurement control section 30, and the like.

Figure 2:
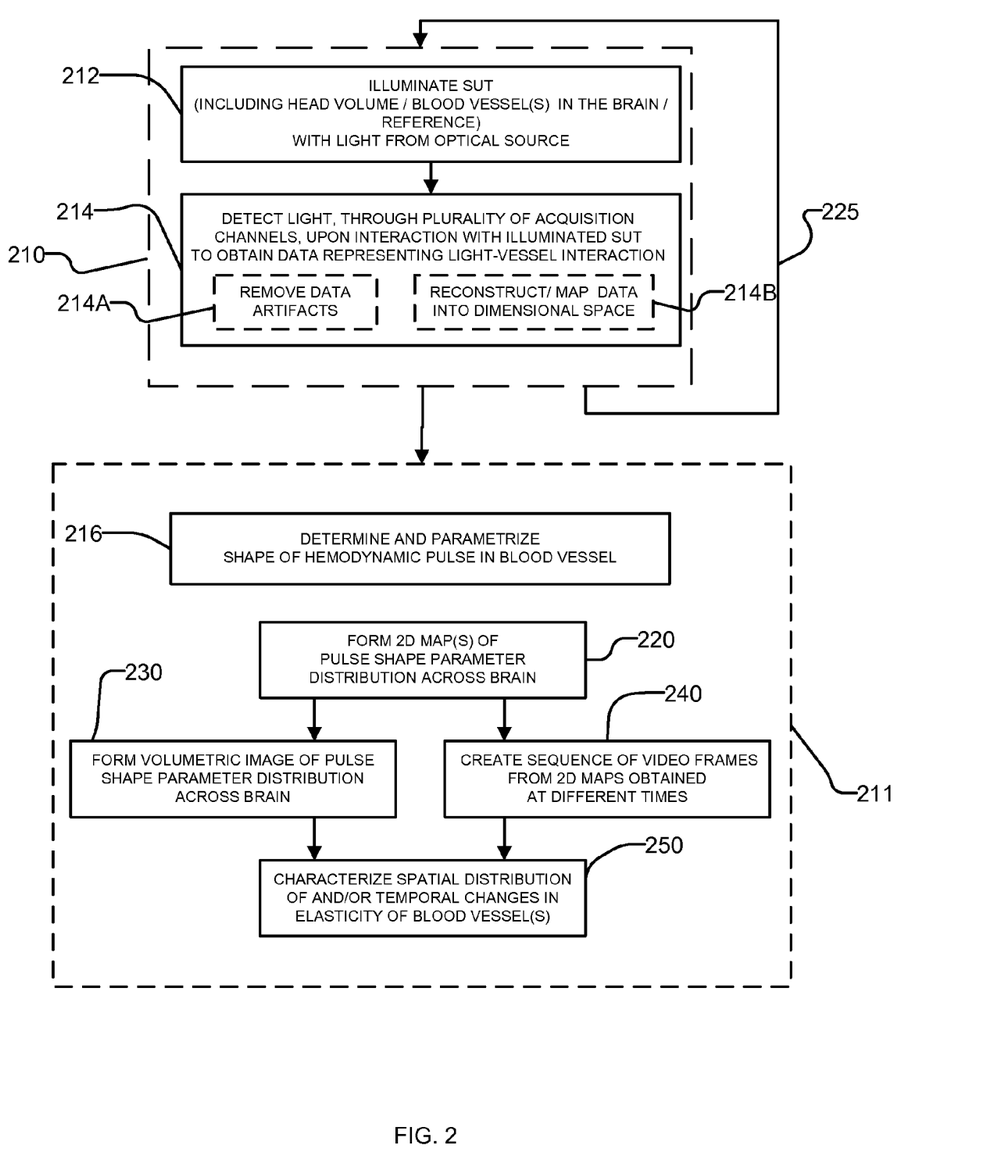
FIG. 2 is a flow chart setting forth the steps of a method for studying the performance of blood vessels in the brain in accordance with one implementation of the present invention.

Turning now to FIG. 2, a flowchart is provided setting forth the steps for a method in accordance with the present invention. The process includes a data acquisition and initial process stage 210 and a post-processing and data analysis stage 211.

Data Acquisition.

The pulse-related data acquisition stage 210 begins with the non-invasive contemporaneous illumination of a chosen volume of the head of the SUT and a reference, such as the carotid artery, for example, with light from light sources. This non-invasive illumination includes illumination of at least one blood vessel such as an artery in the brain, at step 212. During the illumination, the light traversing the illuminated region from a source to an associated detector is detected by that detector and analyzed to determine if the light interacted with this blood vessel, at step 214. The analysis of light-brain region interaction is carried out by determining changes in at least one of the light parameters, such as intensity, for example, upon the propagation through the illuminated region. Generally, an array of optical source/optical detector pairs can be used where each pair effectuates a measurement in a different location of the brain and corresponds to a particular data-acquisition channel.

The pulse-related data are collected using a multichannel optical recording means (such as that or similar to the system described in reference to FIG. 1) that allows recording the data at a minimum of two (but preferably several tens or hundreds) locations on the head of the subject under test (SUT). In one embodiment, the required data can be collected using an Imagent Optical Recording System (manufactured by ISS Inc., Champaign, Ill.) or any similar system configured to generate data representing changes in the intensity of light, such as red or NIR light, propagating through media located between respectively corresponding light sources and detectors disposed in pairs on the surface of the head and separated by some distance (typically several centimeters, for example 2-7 cm) from each other. Similar data need to be acquired from above the carotid in the neck of the SUT. All optical data should be collected with temporal sampling the rate of which appropriately corresponds to the rate of changes in a parameter being determined. For example, the pulse-related data is preferably sample at a rate of at least 30 Hz.

Co-registration. In acquiring the pulse-related data, it may be desirable to co-register the data-collection geometry with the brain anatomy. For example, it is preferred to accurately determine locations of the optical sources and detectors in a fashion that provides a possibility of co-registering and referencing the sources and detectors with respect to the anatomical image of the brain. To this end, a methodology similar to that described by Whalen et al., in *Human Brain Mapping*, v. 29, pp. 1288-1301 (2008), can be used for measurement of the source and location position on the head and co-registration with MRI anatomical images for each SUT. The use of the Whalen methodology in the present application may include the steps of SUT's scalp segmentation using anatomical images of the head surface, marking of scalp to identify fiducial locations such as locations of the attached light sources and detectors, digitization and recording of a structural MRI to identify positions of the markers in the MR images, and coordination of these positions with the results of the scalp segmentation. Alternatively, positions of the sources and detectors could be determined using any like procedure that allows for the accurate spatial correlation, on the spatial scale of a typical head, between the imaged features of the brain and the determined positions with positional errors not exceeding approximately a couple of centimeters on a conventional 3D image of the brain (such as the image produced by the MNI atlas or the Talairach brain atlas). The procedural accuracy less than about one centimeter, appears to limit the quality of the final images.

Refinement and Segmentation. The data collected in acquisition-channel space at step 214 is preferably refined, 214A, to increase the signal-to-noise ratio and contrast of the relevant information by removing any data artifacts associated with the movement of the sensors relative to the head. The refinement can be performed, for example, through detecting and correcting spikes and rapid-onset changes in data with the use of an appropriate statistical algorithm, for example with the use of a moving-window standard deviation. The artifact-free data recorded within a time-window lasting between several seconds and several minutes is further segmented to identify an arterial pulsation with the use of, for example, the adaptive least-square regression algorithm described by Gratton et al. in *Psychophysiology*, v. 32, pp. 292-299 (1995). If several pulsation periods are identified, the different pulsations may be further time averaged to account for the beat-to-beat variability of the heart rate and to improve the reliability of the data-acquisition procedure.

The data sets obtained with the use of different optical acquisition channels are preferably stored separately on a tangible computer-readable storage medium during the averaging procedure. The data set from each channel is represented as time-dependent changes around an average (baseline) level. This representation is achieved by normalizing each data point (i.e., a value registered in a particular acquisition at a particular time) by the average value determined over the entire recording window.

It is appreciated that various non-pulse-related mechanisms can contribute to changing the intensity of light detected in a given acquisition channel on a slow time-scale. Filtering out of these background changes may be accomplished by passing the output of the detectors of the acquisition channels through a high-pass filter. Similarly, to improve the data quality and to increase the signal-to-noise ratio, a low-pass filter can be used. In implementing the filtering of data, however, the data representing the detected light undulations at frequencies between approximately 0.5 and 10 Hz is not filtered, as such filtering may arbitrarily modify the shape of the pulse that will be derived from the filtered data.

Reconstruction. The collected and refined data is further appropriately reconstructed to ascertain changes in pulse characteristics introduced by local conditions (such as inclusions inside the tissue) in a given sub-region of the illuminated volume of the head. In one implementation, the reconstruction procedure transforms or maps the data, representing changes in light intensity that occurred due to interaction between light and brain matter, from "acquisition-channel space" (where the acquired data and time-dependent changes in such data were associated with the optical channels used to acquire the data) to a geometric space, for example a 3D or "voxel" space (where the mapped data and corresponding time-dependent changes of such data are associated with various locations across the illuminated region of the brain). In other words, the result of the data reconstruction (transformation, mapping) into the physical space such as 3D (voxel) space is a data matrix containing the data representing the time-progression of the arterial pulse for each elementary volume (voxel) of the measured space. The reconstruction procedure further facilitates creation of reconstructed 3D (or, alternatively, 2D) images of pulse parameters in physical space that are used, as described below, to characterize spatial distributions of and/or temporal changes in elasticity of brain blood vessel. In another implementation of the reconstruction procedure, the refined data may be mapped from the acquisition-channel space to a 2D physical space, where the information is presented in matrices corresponding to 2D spatial slices or surface renditions across the illuminated volume of the brain. The transformed data is additionally stored in a tangible non-transient computer-readable medium.

Other methods for 2D or 3D reconstruction of changes in light-intensity data are know and suitable. However, many methods vary in their degree of accuracy and complexity of the calculations, and either of these methods can be used for the purposes of the current procedure. In one embodiment of the invention, for example, the method of Feng et al., described in *Applied Optics*, v. 34, pp. 3826-3827 (1995) and characterized by computational simplicity, may be implemented. The method of Feng et al., described in *Applied Optics*, v. 34, pp. 3826-3827 (1995), is incorporated herein by reference.

In a specific embodiment of the invention, to further facilitate comparison of images obtained from different SUTs, the data may be further transformed or mapped from a physical (2D or 3D) space to a standardized space (such as Talairach space or MNI space). Such additional transformation may allow for using the standard anatomical atlases for determination of the location(s) where the changes in arterial elasticity have been observed. It is appreciated, however, that such an additional transformation step does not change the nature of the data-reconstruction procedure and its use in embodiments of the present invention.

Data Analysis.

Figure 3:
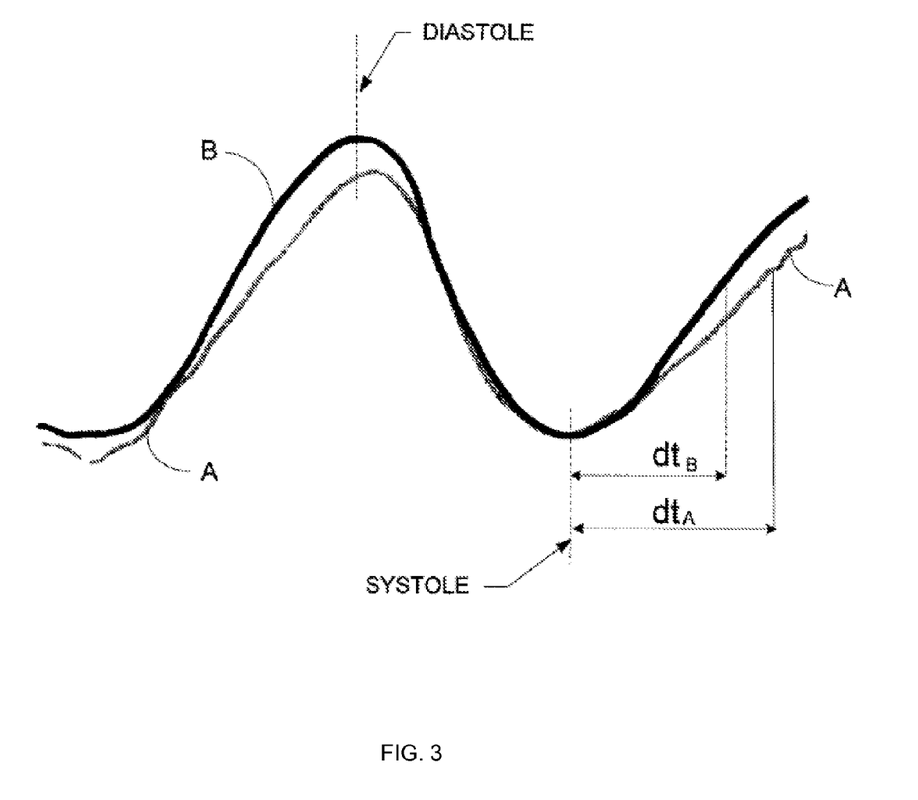
FIG. 3 is a graph that schematically illustrates a difference in latency parameter between an elastic artery (curve A) and a stiff artery (curve B)

Continuing with respect to FIG. 2, based on the reconstructed data representing light-matter interaction, a shape parameter of hemodynamic pulse in a blood vessel or in a section of brain tissue can be determined, at step 216, which relates to the elasticity of the vessel or of the artery or arteries providing blood to the tissue segment. The present invention recognizes that a shape of pulse recovery from systole to diastole is dependent on arterial elasticity. Therefore, the determination of the parameters of the hemodynamic pulse facilitates the determination of the elasticity of a given blood vessel. FIG. 3 provides an additional schematic illustration to this concept. As shown, an individual pulse trace represented by curve A generally corresponds to an elastic artery characterized by a longer duration, $dt_A$, of the systolic phase, while an individual pulse trace represented by curve B corresponds to a stiff artery characterized by a shorter duration, $dt_B$, of the systolic phase. In accordance with an implementation of the present invention, the measurement of a pulse-shape parameter and, particularly, of the parameter dt (such as $dt_A$, $dt_B$) referred to herein as pulse latency takes advantage of the fact that diffuse optical methods such as DOT are highly sensitive to blood pulsation in small blood vessels.

Once the sought after pulse-shape characteristic is determined, it may be further coded or parameterized, 216, by assigning a particular number, determined based on the chosen parameterization rule, to the pulse-shape. As a result of the parameterization, a large number of data points describing the pulse-shape is reduced to a smaller number of parameterized descriptors. Parameterization of the duration of the systolic phase, for example, may include measuring the time required for the pulse to reach a particular level between the systolic and diastolic peaks. Defining this level establishes a criterion for the parameterization procedure. Any parameterization criterion can be used for parameterization, provided that they reflect arterial elasticity (or stiffness), and the choice of the appropriate criterion will depend on its utility to discriminate clinically important conditions.

Figure 4:
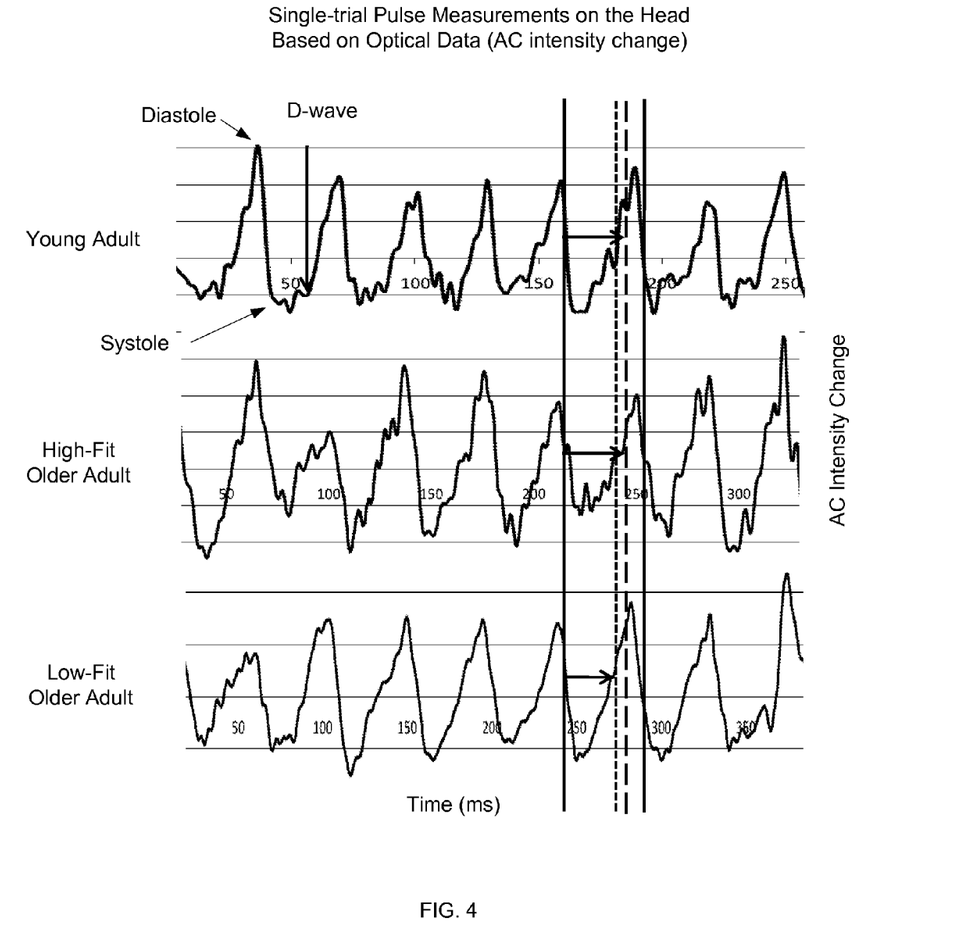
FIG. 4 is a series of graphs demonstrating results of pulse measurements in the brain acquired using the idea of the present invention.

Turning to FIG. 4, examples of individual pulse traces measured with the use of amplitude-modulated light in the brains of one young adult, one high-fit older adult, and one low-fit older adult are shown. Although a modulation of light emitted by an optical source at high, for example exceeding 10 kHz, frequency (that is, the use of AC-light and light-intensity related data) may provide some trade-offs in obtaining the pulse-shape-related data by detecting light that has interacted with a blood vessel (or segment of tissue) within the brain, generally, however, the use of light having substantially constant irradiance or that averaged across the oscillations (referred to as DC-light) does not change the principle of operation of the present invention. The use of DC may, in some cases, be relevant to the 3D reconstruction of the intensity data. In case of light-intensity related data, the systolic phase of the pulse is characterized by a decrease of the light intensity reaching the detector(s), and the diastolic phase is characterized by an increase of the detected light intensity. Specific parameters that can be determined from plots of FIG. 4 include the latency (expressed in milliseconds, for example) of return of blood pressure to the diastolic value after reaching a systole. The higher the value of latency, the more sustained is the pulse, which is indicative of more elastic arteries. Traces of FIG. 4 clearly indicate that the pulse can be well identified on each individual trace (i.e., through one recording channel and in one trial). The data of FIG. 4 also indicate that some of the pulse parameters (such as the duration of the systolic pressure wave, SPW, shown with arrows and related to the d-wave and to the elasticity of the arteries) vary among SUTs.

It is appreciated that the shape of the pulse will vary at different levels within the measured system. For example, the interaction of light with intracranial arteries is reflected in the difference between the shape of the pulse derived from the data measured at the carotid and those obtained from the measurements of the brain. Therefore, simultaneous measurement of the pulse at the carotid and inside the brain affords the derivation of the elasticity of the intracranial arteries.

According to the invention, various other functional parameters related to blood flow in the brain (e.g., systolic wave, diastolic wave, d-wave—a measure of arterial elasticity—duration of the systolic wave that is also sensitive to arterial elasticity) are contemplated to be useful for assessment of cerebrovascular function of the brain. In related embodiments, the data representing any of these parameters may be acquired and ultimately analyzed to describe the function of the brain.

According to the invention and in further reference to FIG. 2, the parameterized data representing the propagation of a hemodynamic pulse in regional arteries (or the propagation of another functional parameter) is presented in the form of maps showing the distribution of the pulse parameter across the measured region of the brain. Accordingly, in the data analysis stage 211, at step 220, the parameterized data representing a shape of the pulse (through at least one pulse-shape parameter such as latency or pulse duration) is transformed into 2D images each of which corresponds to a particular spatial slice through the brain, for example, throughout the cortex.

Figure 5A:
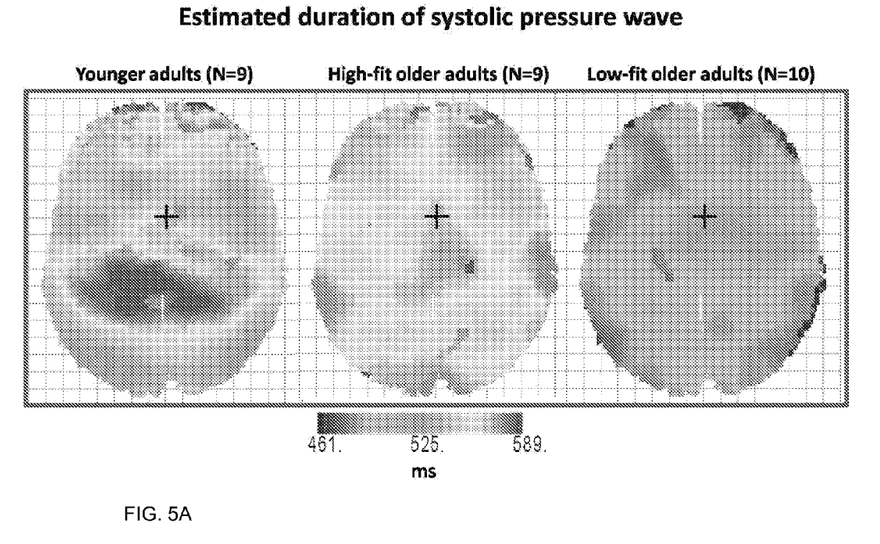
Figure 5B:
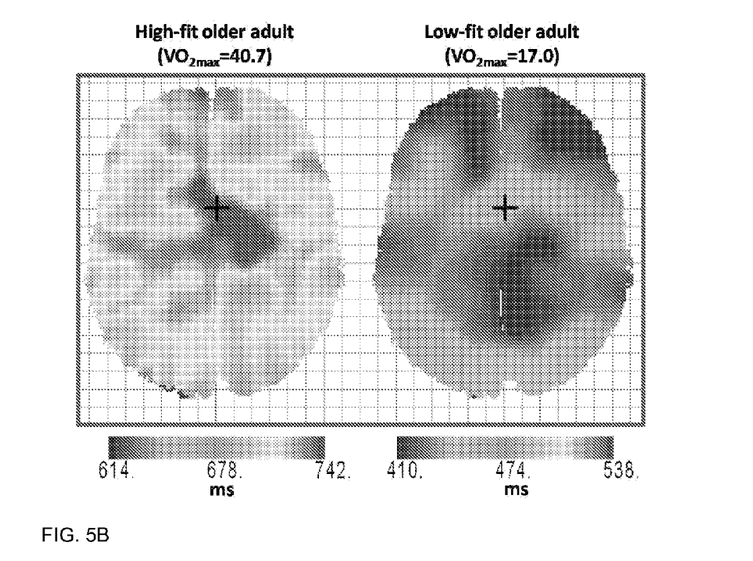
Figure 5C:
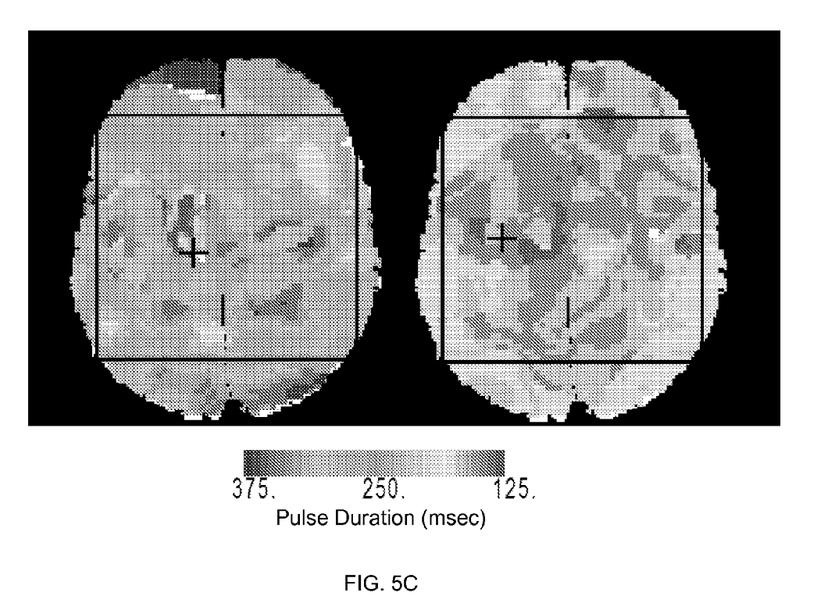

In one embodiment, the derived parameter may be plotted in a color-coded fashion, the color being representative of the parameter values. FIG. 5(A-C) show exemplary 2D images derived from pulse data similar to that of FIG. 4 for young adults and older adults of different fitness levels and mapping the duration of an SPW to locations in the brain. Here, FIG. 5A demonstrates averages for each subject group, while images of FIG. 5B represent the maps for one highly-fit and one lower-fit older adults. FIG. 5C provides additional comparison between the maps of systolic pulse duration for a young subject (on the left) and an old subject (on the right) having similar fitness levels. In deriving a map of FIG. 5C, the parameterization criterion of ⅓ of the distance between the systolic minimum and the diastolic maximum was used. As follows from FIG. 5(A-C), an older low-fit individual has shorter durations of an SPW that corresponds to lower arterial elasticity (or higher arterial stiffness) than that in other subject groups. Map images of a brain obtained with an embodiment of the invention additionally represent regional differences in the duration of the SPW across any given image. These regional differences may be further correlated with likely accumulations of elasticity effects along the arteries that feed corresponding regions of the brain.

Referring again to FIG. 2 and in reference to step 230, a plurality of 2D images formed at step 220 for different brain locations may be optionally combined to form a digital volumetric (3D) image of the duration of an SPW throughout at least a part of volume of the brain. In addition, it may be desirable to provide other clinically useful tools for obtaining the information about the elasticity of brain arteries with the use of the above-described optical imaging methods. For example, it may be desirable to generate a sequence of map images representing the pulse parameter in the same region of the brain taken at different times. To this end, the data acquisition stage 210 of the process of the invention may be repeated, as shown by a temporal loop 225, to collect such time-dependent information regarding localized temporal changes in the arteries. The pulse-related data acquired, refined, reconstructed, and/or parameterized at each temporal loop will be independently stored on a tangible computer-readable medium and further analyzed, at 220 and 230, as discussed above. In addition or alternatively, images of pulse parameter in the same region of the brain taken at different times in a temporal data-acquisition loop 225 may be combined, at step 240, to form a sequence of video frames representing transitory state of brain arteries during the propagation of a hemodynamic wave across that region of the brain, such as the surface of the brain.

Finally, at step 250, the clinical information is extracted by analyzing the images formed at steps 220, 230, and 240 and determining the elasticity of blood vessels based on these images. Therefore, embodiments of the present invention may be used as a potent tool in observing and detecting early prediction of signs of arterial distress and decreased functionality, leading to possible prevention of stroke or other cerebrovascular problems.

Figure 6:
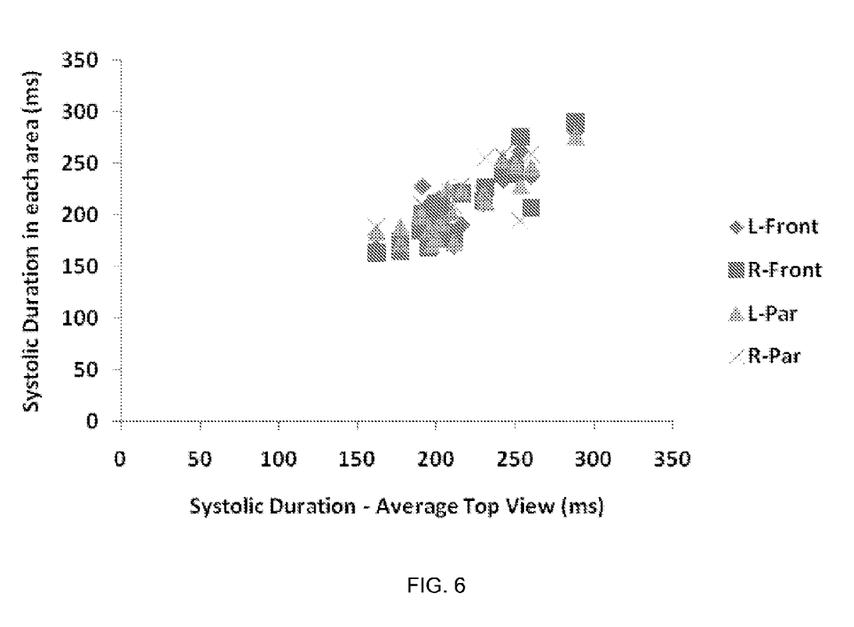
FIG. 6 is a graph that illustrates measures of duration of the systolic phase of the pulse in different regions of the brain for multiple subjects under test, including left frontal, right frontal, left parietal, and right parietal.
Figure 7:
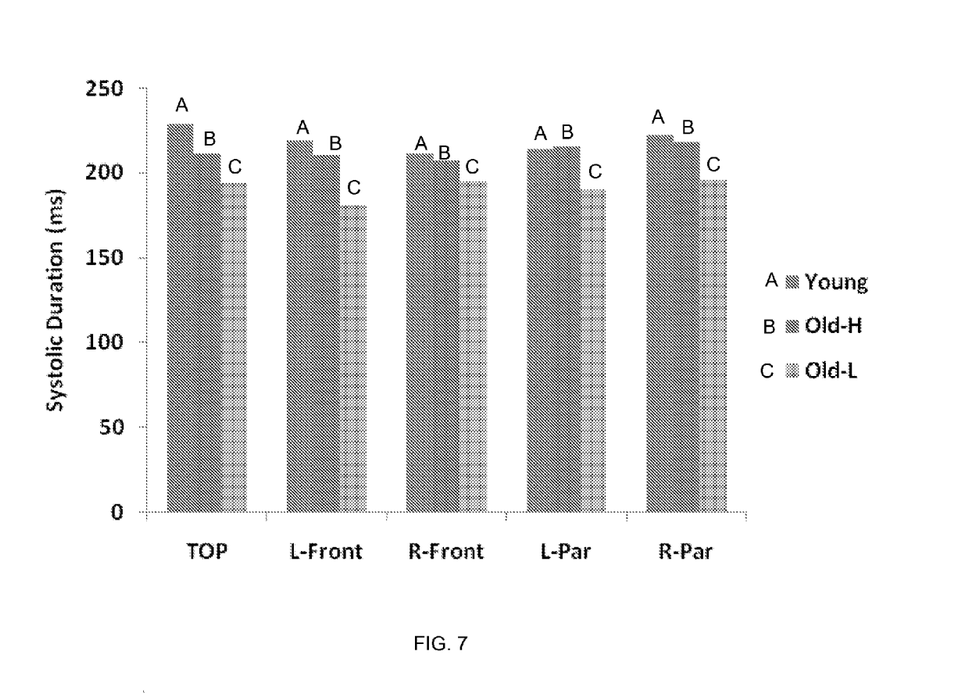
FIG. 7 is a graph that shows duration of systolic phase of the pulse in different brain regions as a function of the subject group.
Figure 8:
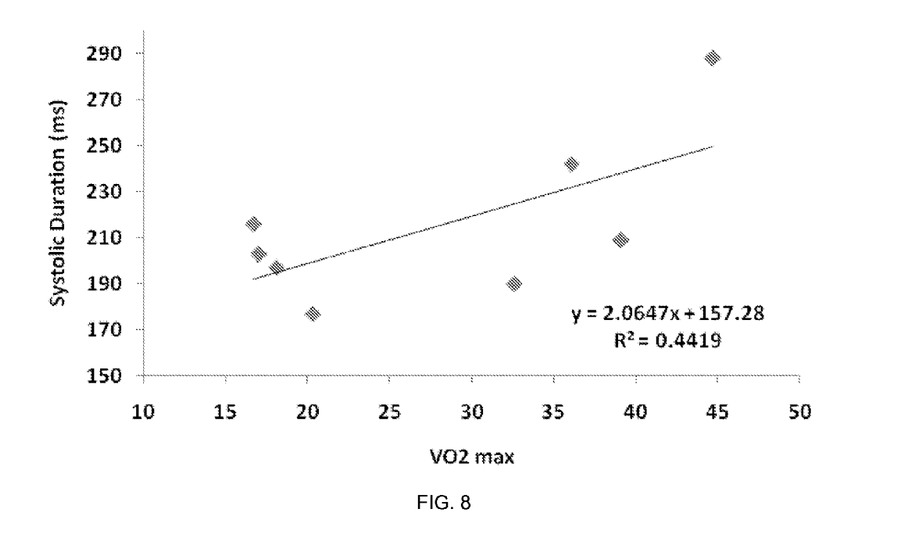
FIG. 8 is a graph that shows correlation of average duration of the systolic pulse phase with the level of physical fitness, VO2max.

In order to provide for clinical evaluation of this type of images or image-maps, the initial determination of values considered "normal" or "abnormal" has to be carried out in normative clinical studies. These normative studies should be conducted separately for different ethnic and age groups. Once these normative studies are conducted, however, the maps can be clinically evaluated by considering the extent to which particular values of the mapped parameter(s) lie within or outside the norm. The definition of normality may vary depending, for example, on the voxel and on the extent to which the tissue contained in the particular measured region reflects different arteries. For instance, brain regions closer to the carotid may show little change in the pulse shape form that observed at the carotid even in normal subjects. Areas of the brain that are remote with respect to the carotid, on the other hand, may exhibit significantly different changes in the pulse shape even in subjects with small degree of arterial stiffness. Further, different SUTs (patients) may show locally abnormal values, reflecting problems with a particular artery. Quantification measures from particular regions of the brain or from the whole brain can also be obtained. To this end, FIGS. 6 and 7, for example, illustrate time durations of the systolic phase obtained from different brain regions in subjects differing in age and physical fitness, indicating the reliability of data and the consistency of difference in data among the groups such as young subjects (between 18-30 years of age), subjects older than 65 years of age with high fitness level (VO2max>25), and subjects older than 65 years of age with low fitness level (VO2max<25). FIG. 8 shows the relationship between the time duration of the systolic phase and physical fitness in old subjects.

Embodiments of the invention described above are intended to be merely exemplary; numerous variations and modifications will be apparent to those skilled in the art. All such variations and modifications are intended to be within the scope of the present invention.

It is contemplated that the above-discussed image maps that are representative of the cerebrovascular function and performance of the brain can be also obtained, in accordance with the method of the invention, by measuring other characteristic of light propagating through the illuminated region. For example, in an alternative implementation of the method of the invention a phase delay associated with interaction of light and a blood vessel can be measured if frequency-domain optical imaging instruments are used. It is recognized that the use of phase-delay-based measurement and the following analysis of the acquired phase-delay data in either the frequency domain or the time domain may allow for characterization of properties of the biological tissue located deeper in the brain than that characterized with a measurement utilizing light intensity parameters. In another related embodiment, the measured data may be used for determination of oxy and/or decoy-hemoglobin concentrations, thereby providing an alternative venue for characterizing the cerebrovascular activity of the brain. In yet another embodiment, different pulse parameterization methods can be used that include curve-fitting methods as well as methods based on the statistical comparison of the pulse shape in different clinical populations.

The sought after informative parameter (such as the shape of the pulse) obtained for each spatial element (voxel) of the illuminated portion of the brain can be influenced by both intracranial and extracranial (i.e., systemic) factors. Specifically, it may be influenced by both heart and carotid factors as well as by stiffness of the intracranial arteries. It is, therefore, useful to compare the shape of the pulse at the carotid with that of the pulse observed within the brain. For instance, the same parameter can be computed for the carotid pulse and the pulse measured in each voxel within the brain. This comparison may be used to isolate intracranial effects (for instance, by subtraction, or some other mathematical or statistically-derived operation).

Brain images obtained with the use of an embodiment of the invention can be combined with and referenced with respect to other measures of hemodynamic brain function. Accordingly, a concurrent recording and storing, on tangible storage medium, of brain images with different technical modalities, such as MRI is also contemplated, for example, with target regions of interest in the frontal cortex. Therefore, a system and method is provided that provides more comprehensive coverage of the brain than traditional systems and methods. For example, the present invention allows a user to automatically generate an image of the cerebrovascular parameters across the brain, whereas a conventional ultrasound-based competing technology (TCD) relies on a trained user who listens to the outputs affected by blood flow. Also, the present invention provides improved, millisecond-level time resolution, as compared to MRI. Further more, the present invention enables early diagnosis of cerebrovascular problems. Unlike any of the existing methods, the present invention offers a tool for early diagnosis and monitoring of cerebrovascular problems through measurement of elasticity of arteries in the brain. Additionally, the embodiments of the method of the invention are more cost-efficient than traditional analysis methods employing MRI and PET.

What is claimed is:

1. An imaging system comprising:
    an illumination system configured to illuminate a region of interest (ROI) of a brain of a subject under test (SUT), the ROI having at least one blood vessel, and a reference blood vessel with photons and receive the photons after interaction with the ROI and the reference blood vessel;
    a light detection mechanism including an optical detector and a signal processing section, the light detection mechanism configured to acquire the photons after interaction thereof with the ROI and the reference blood vessel to compile first imaging data representing the ROI and second imaging data representing the reference blood vessel;

a processor, in operable communication with the light detection mechanism, configured to process the first and second imaging data to determine a first shape parameter of a hemodynamic pulse in the at least one blood vessel and a second shape parameter of a hemodynamic pulse in the reference blood vessel;

a display section, in which appears a display of at least one image representing the first shape parameter of a hemodynamic pulse in the at least one blood vessel; and tangible, non-transitory storage medium containing program code which, when downloaded on said processor, causes the processor to determine the first shape parameter from processing of the first imaging data;

to determine the second shape parameter based on processing of the second imaging data;

to compare said first and second shape parameters to determine a difference therebetween;

to transform the first imaging data to create said at least one image showing a distribution of the first shape parameter in a cross-section of the ROI; and to form output data representing elasticity of said at least one blood vessel from the ROI based on said difference and said at least one image.

2. An imaging system of claim 1, wherein the at least one image is two-dimensional.

3. An imaging system of claim 1, further comprising a digital filter with a pass-band from about 0.5 Hz to about 10 Hz configured to refine the imaging data obtained at all frequencies within said pass-band.

4. An imaging system according to claim 1, wherein the first shape parameter of a hemodynamic pulse in the at least one blood vessel includes a hemodynamic pulse latency.

5. An imaging system according to claim 1, wherein the illumination system contains at least one acquisition channel defined by a pair of a light source emitting the photons and the optical detector receiving the photons, and a portion of the ROI separating the light source and the optical detector, wherein a location of said optical detector on a head of the SUT is co-registered with anatomy of the brain.

6. An imaging system of claim 1, wherein said program code causes the processor to compare said first and second shapes as a function of time to form output data representing temporal changes in elasticity of said at least one blood vessel.

7. An imaging system of claim 1, wherein said program code causes the processor to determine said first shape of a hemodynamic pulse in said at least one blood vessel of the ROI based on a hemodynamic pulse latency that represents a prolongation of a systolic phase of a corresponding hemodynamic pulse with respect to a diastolic phase thereof.

8. An imaging system of claim 1, wherein said first shape parameter of a hemodynamic pulse in the at least one blood vessel represents elasticity of said at least one blood vessel of the ROI.

9. A computer program product for use on a computer system having a processor configured to create an image of a region of a brain of a subject under test based on input digital data that includes first data representing interaction between light and at least one blood vessel in said region and second data representing interaction between light and a reference blood vessel of the subject under test, the computer program product comprising a computer-usable tangible medium having a computer readable program code therein, which, when loaded into the computer system, causes the processor:

to determine, from said input digital data, a first shape parameter of a hemodynamic pulse in said at least one blood vessel;

to transform said input digital data to produce an output representing an image of said first shape parameter across said region;

to determine, from said input digital data, a second shape parameter of a hemodynamic pulse in the reference blood vessel;

to compare said first and second shape parameters to define a difference therebetween; and based on said difference and said image, to produce an output representing elasticity of said at least one blood vessel of said region.

10. A computer program of claim 9, wherein the computer-usable tangible medium further contains program code that causes the processor to compare a duration of a systolic phase of said hemodynamic pulse in said at least one blood vessel with a duration of a diastolic phase thereof to determine a prolongation of the systolic phase with respect to the diastolic phase.

11. An imaging system operable to produce output data representing elasticity of at least one blood vessel of a brain of a subject under test (SUT), the system comprising:

an illumination system configured to generate photons and to illuminate non-invasively a region of interest (ROI) of said brain with said photons and receive the photons after interaction thereof with the ROI having at least one blood vessel; and to illuminate non-invasively, and contemporaneously with illumination of said ROI, a reference blood vessel with said photons and receive the photons after interaction thereof with said reference blood vessel;

a light detection mechanism including an optical detector and a signal-processing section, the light detection mechanism configured (i) to acquire photons that have been received after interaction with the ROI to compile first imaging data representing a hemodynamic pulse in said at least one blood vessel from the ROI; and (ii) to acquire photons that have been received after interaction with the reference blood vessel to compile second imaging data representing a hemodynamic pulse in said reference blood vessel;

a processor in operable communication with the light detection mechanism, the processor programmed to determine a first shape of said hemodynamic pulse in said at least one blood vessel from said first imaging data;

to determine a second shape of said hemodynamic pulse in said reference blood vessel from said second imaging data;

to compare said first and second shapes to determine a difference therebetween;

to form said output data representing elasticity of said at least one blood vessel from the ROI based on said difference; and to create at least one image of elasticity distribution based on at least said first imaging data; and a display section, in which appears a display of a visually-perceivable representation of at least one of the first imaging data, the second imaging data, the output data, and said ROI.

12. An imaging system of claim 11, wherein said first and second imaging data contain data representing time-progressions of respectively corresponding arterial hemodynamic pulses.

13. An imaging system of claim 11, wherein a determination of said difference includes a determination of a hemodynamic pulse latency representing a prolongation of a systolic phase of a corresponding hemodynamic pulse with respect to a diastolic phase thereof.

14. An imaging system of claim 11, wherein the processor is further programmed to parameterize a shape, from the first and second shapes, based on assigning a number of parameterized descriptors to a number of data points describing said shape, wherein said number of parameterized descriptors is smaller than said number of data points, and wherein said parameterized descriptors represent elasticity of an artery.

15. An imaging system of claim 11, wherein said display section provides a time-evolution of spatial maps of said first shape across the ROI.

16. An imaging system of claim 11, wherein said processor is further programmed to transform the first imaging data to generate said at least one image of elasticity distribution showing a distribution of the first shape parameter in a cross-section of the ROI and to form said output data representing elasticity of said at least one blood vessel from the ROI based on said difference and said at least one image of elasticity distribution.

\* \* \* \* \*